United States Patent
McWeeney (10) Patent No.: US 8,142,386 B2
(45) Date of Patent: Mar. 27, 2012

(54) ANTI-REFLUX URETERAL STENTS AND METHODS

(75) Inventor: John O. McWeeney, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1321 days.

(21) Appl. No.: 11/052,099

(22) Filed: Feb. 8, 2005

(65) Prior Publication Data

US 2005/0149201 A1 Jul. 7, 2005

Related U.S. Application Data

(63) Continuation of application No. 10/125,273, filed on Apr. 18, 2002, now Pat. No. 6,908,447.

(51) Int. Cl.
*A61F 2/04* (2006.01)
*A61F 2/94* (2006.01)

(52) U.S. Cl. .......................... 604/9; 623/23.68

(58) Field of Classification Search ...... 623/23.68–23.7; 604/9
See application file for complete search history.

(56) References Cited

U.S. PATENT DOCUMENTS

| | | | |
|---|---|---|---|
| 4,225,979 A | 10/1980 | Rey et al. | |
| 4,334,327 A | 6/1982 | Lyman et al. | |
| 4,790,809 A | 12/1988 | Kuntz | |
| 5,019,102 A | 5/1991 | Hoene | |
| 5,052,998 A | 10/1991 | Zimmon | |
| 5,599,291 A | 2/1997 | Balbierz et al. | |
| 5,647,843 A | 7/1997 | Mesrobian et al. | |
| 5,766,209 A | 6/1998 | Devonec | |
| 5,782,916 A | 7/1998 | Pintauro et al. | |
| 5,964,744 A | 10/1999 | Balbierz et al. | |
| 5,971,967 A | 10/1999 | Willard | |
| 5,984,965 A | 11/1999 | Knapp et al. | |
| 5,989,207 A | 11/1999 | Hughes | |
| 6,063,119 A | 5/2000 | Pintauro et al. | |
| 6,071,292 A | 6/2000 | Makower et al. | |
| 6,132,364 A | 10/2000 | Rottenberg et al. | |
| 6,168,614 B1 | 1/2001 | Andersen et al. | |
| 6,610,046 B1 * | 8/2003 | Usami et al. | 604/530 |
| 6,908,447 B2 | 6/2005 | McWeeney et al. | |
| 2001/0053936 A1 | 12/2001 | Whitmore, III | |
| 2002/0173754 A1 * | 11/2002 | Whitmore, III | 604/264 |

FOREIGN PATENT DOCUMENTS

| | | | |
|---|---|---|---|
| DE | 44 15 252 A1 | * | 11/1995 |
| DE | 19806507 A1 | | 8/1999 |
| FR | 2 248 015 | * | 5/1975 |
| JP | 8-308933 A | * | 11/1996 |

(Continued)

OTHER PUBLICATIONS

English translation of Fujiwara et al., JP 8-308933 A, published on Nov. 26, 1996.*

(Continued)

*Primary Examiner* — David H. Willse (57) ABSTRACT

An anti-reflux ureteral stent includes an elongated member with a distal end having a first retention structure and a proximal end having a second retention structure. A lumen extends between the distal and proximal ends. The elongated member may include a valve near the proximal end and distal to the second retention structure. The valve may include one or more slits or windows tending to render the elongated member collapsible. The valve may include one or more protrusions to partially occlude the lumen. A protrusion, if present, may be shaped as a helical thread. The second retention structure may be shaped as a barb to engage a ureteral orifice in a bladder.

27 Claims, 10 Drawing Sheets

FOREIGN PATENT DOCUMENTS

SU            1191075 A  *  11/1985
WO     WO 02/098500 A1    12/2002

OTHER PUBLICATIONS

English translation of Popov, SU 1191075 A (Nov. 15, 1985).*

Communication Relating to the Results of the Partial International Search for International Patent Application No. PCT/US03/11879, 4 pages, Dec. 10, 2003.

International Search for International Patent Application No. PCT/US03/11879, 5 pages, Dec. 10, 2003.

* cited by examiner

ANTI-REFLUX URETERAL STENTS AND METHODS

This application is a continuation application of application Ser. No. 10/125,273, filed on Apr. 18, 2002, now U.S. Pat. No. 6,908,447, the entire content of which is herby incorporated by reference.

TECHNICAL FIELD

This invention generally relates to medical devices for drainage of fluids, and more specifically to anti-reflux medical devices for drainage of fluids.

BACKGROUND INFORMATION

Drainage devices or stents may be used to treat or avoid obstructions in fluid passageways due to ureteral tumors that disrupt the flow of urine from the kidneys to the bladder. They also may be used to strengthen a compromised vessel such as a ureteral wall. Ureteral stents typically are tubular in shape, terminating in two opposing ends: a kidney distal end and a bladder proximal end. One or both of the ends may be curved in a pigtail or J-shape to prevent the migration of the stent due, for example, to physiological movements.

SUMMARY OF THE INVENTION

Stents may cause or contribute to significant patient discomfort. One problem associated with ureteral stents is bladder pain attributed to stent contact with the trigone area of the bladder, particularly when the stent extends through the ureteral orifice and into the bladder. The region known as the trigone or trigonum is a triangular-shaped region located on the floor of the urinary bladder between the opening of the urethra in front and the two ureters at the sides. The trigone is believed to be particularly innervated and sensitive to the presence of any foreign bodies such as stent members. Another problem associated with ureteral stents is flank pain caused by urine reflux that occurs when urine travels from the bladder to the kidneys in response to retrograde pressure. Retrograde pressure occurs in the bladder when attempting to void the bladder of urine, and may transmit urine or other fluids up the stent to the kidney. The rigidity of even relatively soft ureteral stents may also irritate the intramural tunnel (the lower 1-2 cm of the ureter prior to its entry into the bladder). In the absence of a stent, the intramural tunnel closes during voiding of the bladder; the presence of a stent may interfere with this closure, irritating the intramural tunnel and permitting urine reflux.

The present invention concerns a ureteral stent designed to reduce patient discomfort generally caused by stents contacting the trigone or by urine flowing up the stent toward the kidney. Thus, increased comfort may be gained by reducing the size of the retention structure at the bladder (proximal) end of the stent. Patient discomfort can be minimized by reducing the amount of contact with the trigone. Valves and other structures can minimize flank pain by interrupting urine backflow up the stent toward the kidney without preventing drainage of urine from the kidney to the bladder. Modifying that portion of the stent residing in the intramural tunnel to render that portion deformable or collapsible can ease closure of the intramural tunnel during voiding of the bladder, reducing intramural tunnel irritation and urine reflux. In all aspects of the following invention descriptions, all members have a distal retention end structure, the purpose of which is to prevent downward migration of the stent from kidney to bladder and maintain the proximal retention structure to be as close to the ureteral orifice as possible.

In one aspect, the invention relates to a ureteral stent including an elongated member having a distal end with a first retention structure and a proximal end with a second retention structure. A lumen extends between the proximal and distal ends of the elongated member. The elongated member includes a valve positioned near the proximal end, but distal to the proximal retention structure. The valve is preferably between about one centimeter to about four centimeters (more preferably at about two centimeters) from the proximal retention structure. The distance of the valve from the proximal retention structure is measured from that portion of the proximal retention structure that, in use, contacts the ureteral orifice and restrains further movement of the elongated member towards the kidney; the distance is therefore the distance from the valve to the ureteral orifice when the stent is in use. Where applicable, the middle of the valve (e.g. the middle of a slit, window, etc.) is considered to be the position of the valve for measuring purposes. The elongated member should be long enough such that when the stent is in a human ureter, the distal end may reside in a kidney and the proximal end in the bladder. The elongated member preferably has a plurality of openings permitting fluid access to the lumen.

The valve may include a slit or a window in a wall of the elongated member. The slit or window may be at least one centimeter long. The valve may include a plurality of slits or windows. For example, the valve may include two windows, or three parallel slits.

The valve may also include a flap extending from a wall of the elongated member. For example, the valve may include at least two flaps extending proximally from the wall and positioned such that the flaps are in contact with one another, closing the valve, when fluid pressure from the proximal (bladder) end is greater than the pressure from the distal (kidney) end. When fluid pressure from the distal end exceeds the pressure from the proximal end, the flaps separate, opening the valve.

The proximal retention structure may include a hydrophilic polymer that expands upon hydration and may be shaped, for example, as a cylinder. The hydrophilic polymer may be, for example, polyurethane, nylon, polycarbonate, poly(ethylene oxide), polyvinyl pyrrolidone, polyvinyl alcohol, poly(ethylene glycol), polyacrylamide, poly(hydroxyethylacrylate), or copolymers thereof.

In another embodiment, the invention relates to a ureteral stent including an elongated member having a distal end with a first retention structure, a proximal end with a second retention structure, and an inner surface defining a lumen between the distal and proximal ends. One or more protrusions extend from the inner surface into the lumen to partially occlude the lumen. The one or more protrusions are shaped and positioned to introduce turbulence into urine flow from the proximal end during voiding of the bladder when the distal end is in a kidney and the proximal end in a bladder, reducing urine reflux. The one or more protrusions permit urine flow from the kidney to the bladder at other times. The one or more protrusions may be rigid, and preferably reduce the hydraulic radius by a factor of at least two, three, or four.

In yet another embodiment, the invention relates to a ureteral stent including an elongated member having a distal end with a first retention structure, a proximal end with a second retention structure, and an inner surface defining a lumen between the distal and proximal ends. A portion of the inner surface between the distal and proximal ends includes a helical thread having a height extending into the lumen. The height of a proximal portion of the thread may exceed the height of a distal portion of the thread. Preferably, the lumen has a substantially circular cross-section and the height of a proximal portion of the thread is greater than the radius of the lumen. The helical thread may include a proximally-facing wall forming a 90 degree angle with the inner surface; the angle may be sharp-edged or round-edged. In a preferred embodiment, a proximally-facing wall and a second wall of the helical thread form a sharp-edged angle no greater than about 90 degrees. The helical thread may include a distally-facing wall forming an angle of no more than 90 degrees with the inner surface.

In another aspect, the invention relates to a method of promoting ureteral urine flow. The method includes the steps of providing a ureteral stent and introducing it into a ureter. The stent has a distal end with a retention structure and a proximal end with a barb. The stent is introduced into the ureter such that the distal end of the stent is in a kidney and the proximal end is in the bladder. The barb engages the ureteral orifice of the ureter to prevent distal migration of the ureteral stent out of the bladder.

In another embodiment, the invention relates to a method of promoting ureteral urine flow without undue bladder irritation. The method includes the steps of providing a ureteral stent and introducing it into a ureter. The stent has a distal end with a first retention structure and a proximal end with a second retention structure. The stent is introduced such that the distal end of the stent is in a kidney and the proximal end in the bladder. The proximal end of the ureteral stent extends less than two centimeters into the bladder.

In yet another embodiment, the invention relates to a method of promoting ureteral urine flow while minimizing intramural tunnel irritation. The method includes the steps of providing a ureteral stent and introducing it into a ureter. The stent has a compressible portion between a distal end with a first retention structure and a proximal end with a second retention structure. The proximal end may be positioned in a bladder, and the distal end may be positioned in a kidney. The stent is preferably positioned in a patient such that the compressible portion is in an intramural tunnel, permitting compression of the stent by the intramural tunnel during voiding of the bladder.

In still another embodiment, the invention includes a method for promoting ureteral urine flow from a kidney to a bladder. The method includes the steps of providing a ureteral stent and introducing it into a ureter. The ureteral stent includes an elongated member having a distal end with a first retention structure and a proximal end with a second retention structure. The elongated member also has an inner surface defining a lumen between the distal and proximal ends. The inner surface has one or more protrusions that extend into and partially occlude the lumen. The one or more protrusions disrupt urine flow from the bladder during voiding of the bladder, thereby reducing reflux, while permitting urine flow from the kidney to the bladder at other times. The stent is preferably positioned in a patient with the distal end in a kidney and the proximal end in the bladder.

In a preferred embodiment, the invention includes a method of promoting ureteral urine flow from a kidney to a bladder. The method includes the steps of providing a ureteral stent and introducing it into a ureter. The stent includes an elongated member having a distal end with a first retention structure and a proximal end with a second retention structure. The elongated member also has an inner surface defining a lumen between the distal and proximal ends. A portion of the inner surface includes a helical thread having a height extending into the lumen. A height of a proximal portion of the thread is greater than the height of a distal portion of the thread. The stent may be positioned with the distal end in a kidney, and may be positioned with a proximal end in the bladder. The stent is preferably positioned such that the height of the thread is greater in a portion of the thread toward the proximal end of the stent, discouraging urine reflux from the bladder to the kidney and permitting urine drainage from the kidney to the bladder.

The foregoing and other aspects, embodiments, features, and advantages of the invention will become apparent from the following description, figures, and claims.

BRIEF DESCRIPTION OF THE DRAWINGS

The drawings are not necessarily to scale, emphasis instead generally being placed upon illustrating the principles of the invention.

FIGS. 5A-B depict exemplary ureteral stents with flap valves.

DESCRIPTION

This invention generally concerns a ureteral stent that significantly reduces discomfort to a patient when positioned within a patient's ureter. The devices and methods of the present invention increase patient comfort by minimizing the degree of contact of the device with the trigone region, by providing a deformable or collapsible stent portion in the intramural tunnel, and/or by reducing or eliminating reflux of liquid to the kidneys from the bladder.

Figure 1A:
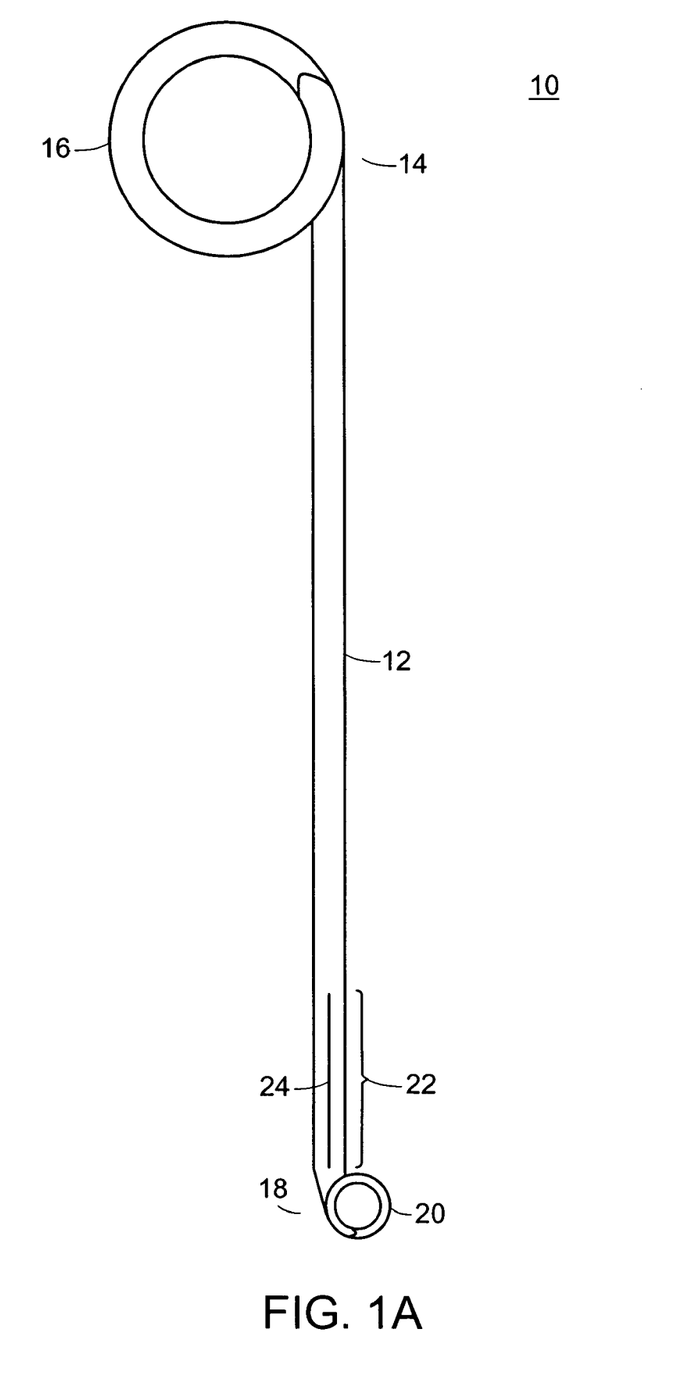
FIG. 1A depicts an exemplary embodiment of a ureteral stent of the invention with a slit valve in the elongated member and a pigtail at the proximal end.

Referring to FIG. 1A, ureteral stent 10 includes elongated member 12 having distal end 14 with first retention structure 16, depicted as a first pigtail. Elongated member 12 also includes proximal end 18 with second retention structure 20, depicted as a second pigtail. As will be further elaborated below, first retention structure 16 and second retention structure 20 may instead have other shapes suitable to stabilize the stent within the ureter, such as a hook or J-shape, barbs, protrusions, and the like. A lumen (not shown) extends between proximal end 18 and distal end 14; ureteral stent 10 also generally includes a plurality of openings (not shown) providing fluid access to the lumen. The cross-sectional geometry of the stent and the lumen may be any shape that allows liquid flow including, for example, round, oblong, elliptical, hexagonal, D-shaped, crescent-shaped and square.

The ureteral stent may be formed of a biocompatible plastic or polymer such as ethylene vinyl acetate (EVA), polytetrafluoroethylene (PTFE), silicone polyurethane, polyamide, polyurethane plastics, polyethylene plastics, and other thermoplastics and block copolymers thereof, for example. The polymer may have a Shore hardness between about 60 A and about 85 A, or alternately between 20 Shore D and 65 Shore D.

The ureteral stents may have walls of constant or varying thickness. Preferably, portions of the walls near the distal end are sufficiently thick to be kink-resistant despite constriction or other manipulation of the stent due to enlargement of tissue surrounding it or peristaltic motions, and during insertion and removal of the device into and out of the body. A kink-resistant stent wall has an annular wall that does not collapse upon itself upon radial or lateral pressure of the surrounding body tissues when positioned to drain a body cavity of a mammal or upon longitudinal pressure exerted during insertion of the stent. A wall may be rendered sufficiently kink-resistant by varying the thickness of the wall of the stent; appropriate wall thickness depends on the softness or sturdiness of the material used to manufacture the stent. For example, a thickness of from about 0.008 inches to about 0.03 inches may be used with materials such as silicone, EVA, PTFE, polyurethane plastics, polyethylene plastics, and copolymers thereof. The inner diameter may be between about 0.035 inches to about 0.12 inches, preferably between about 0.035 inches and 0.075 inches, and more preferably is about 0.06 inches. The outer diameter may be between about 0.05 inches and about 0.12 inches, preferably between about 0.05 inches and about 0.1 inches, and more preferably is about 0.09 inches.

Figure 1B:
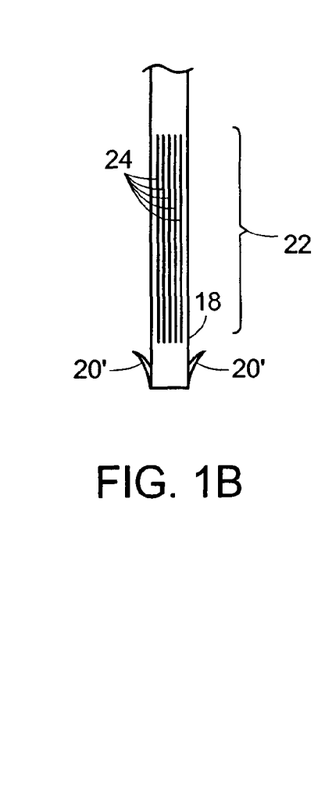
FIG. 1B depicts the proximal portion of another exemplary embodiment with a plurality of slits in the elongated member and a barb at the proximal end.

In the preferred embodiment shown in FIG. 1A, valve 22 is located on the elongated member near proximal end 18 but distal to second retention structure 20. Valve 22 preferably includes a deformable wall with at least one longitudinal slit 24 which traverses a wall of elongated member 12 and extends from the exterior surface of the wall to the interior surface bordering the lumen. Slit 24, if present, is preferably at least one centimeter long, and is more preferably about two centimeters long. As shown in FIG. 1B, valve 22 may alternatively include a plurality (e.g. three or more) of parallel slits 24. Valve 22 is preferably positioned at a distance from second retention structure 20 by about zero juxtaposition) to about four centimeters.

Figure 2A:
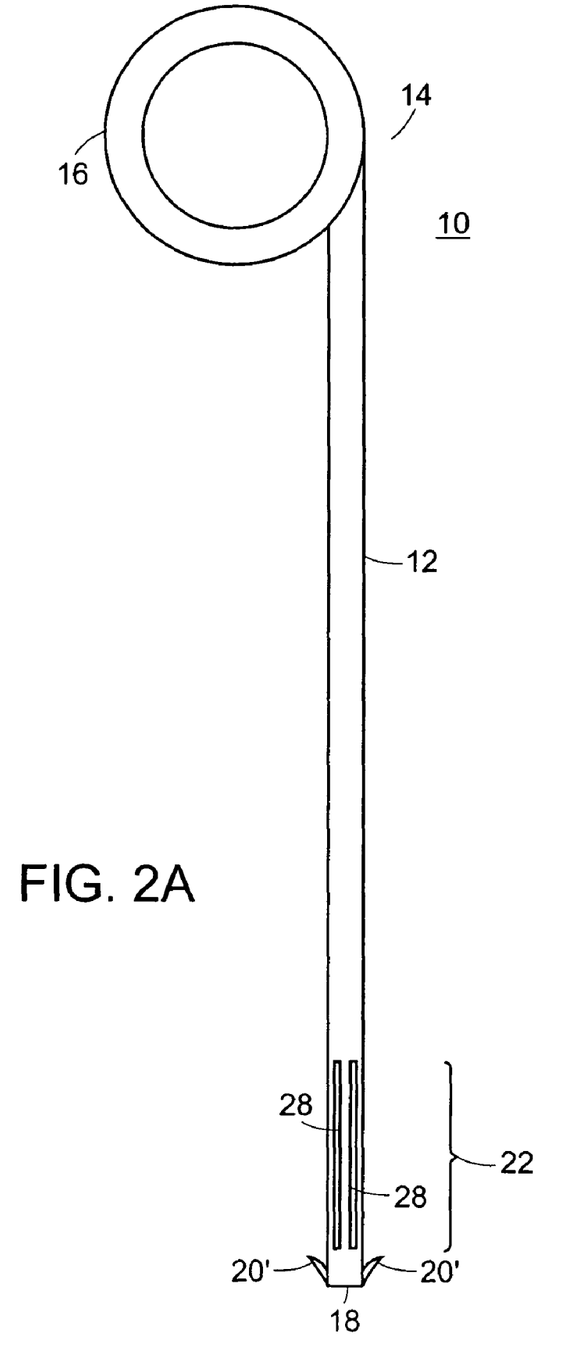
FIGS. 2A-2D depict exemplary ureteral stents with window valves.
Figure 2B:
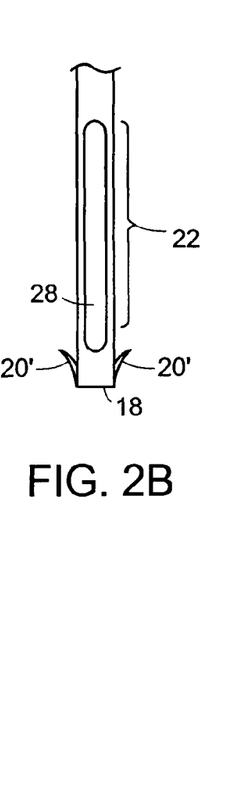
Figure 2C:
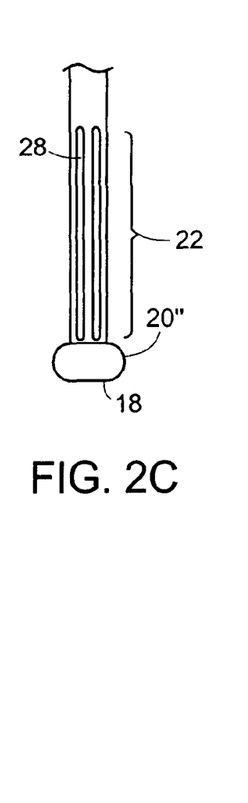
Figure 2D:
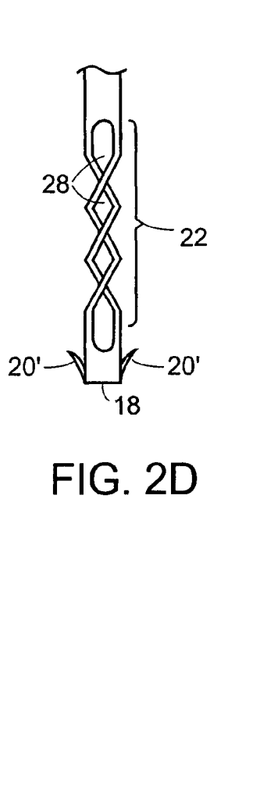

Referring to FIGS. 2A-D, valve 22 may instead include a deformable wall with one or more (e.g. two) windows 28 traversing the wall of elongated hollow member 12. The window or windows 28 are preferably at least one centimeter long and are more preferably about two centimeters long. Proximal end 18 of elongated member 12 may include a second retention structure. The retention structure may include one or more barbs 20' (FIGS. 2A, 2B, 2D); a structure 20'' having an outer dimension W, perpendicular to the longitudinal axis of elongated member 12, that is greater than the outer diameter of the elongated member 12 (FIG. 2C, shown with rounded edges), or a pigtail as in FIG. 1A. Furthermore, elongated hollow member 12 may be twisted about its longitudinal axis in the vicinity of valve 22 as shown in FIG. 2D, facilitating fluid flow through the window or windows 28 and potentially reducing the effective diameter of that portion of elongated hollow member 12.

A second retention structure 20 may be formed by skiving elongated member 12 to form a barb 20' (FIGS. 2A, 2B, 2D), or by molding a barb from, for example, a silicone flap. A barb, if present, is preferably no more than about 4 mm long.

Figures 3, 3A:
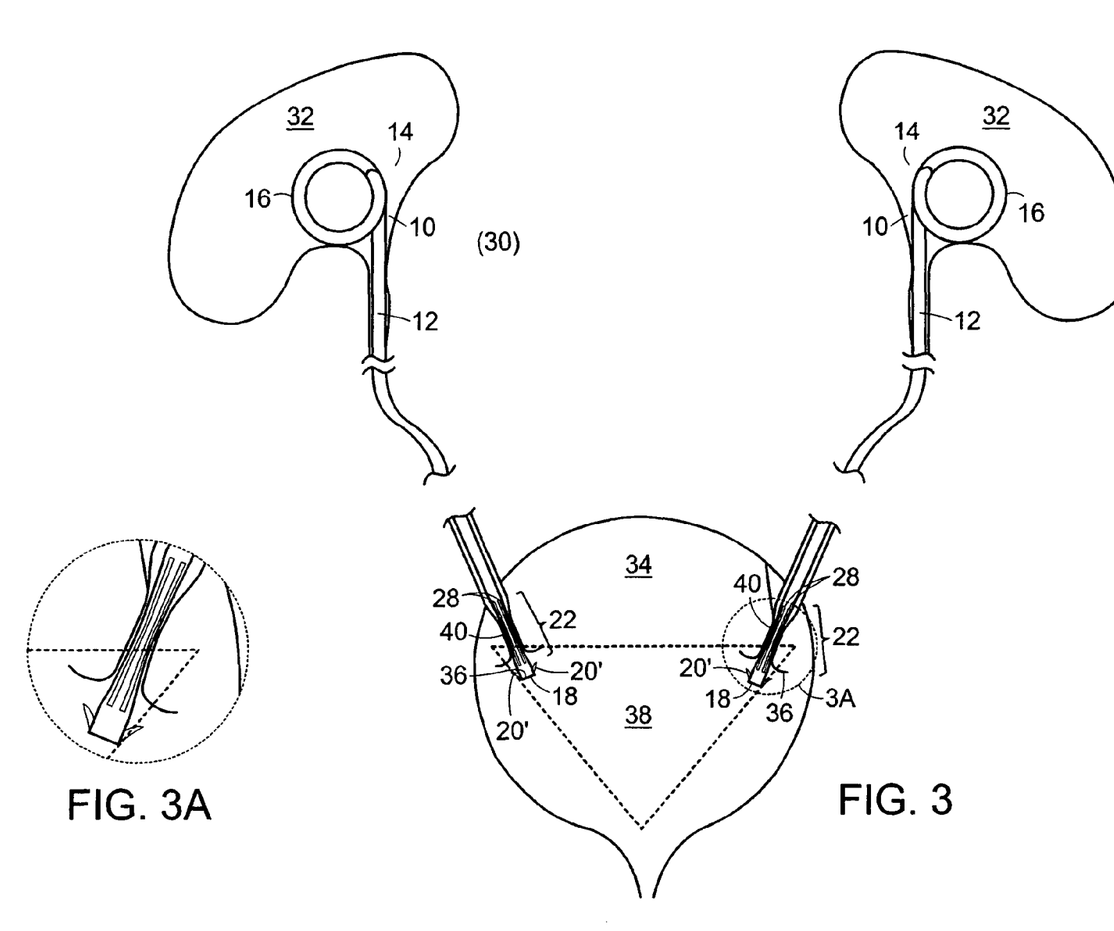
FIG. 3 depicts a pair of the ureteral stents of FIG. 2A implanted in a pair of mammalian ureters.
FIG. 3A is magnified view of a portion of a ureteral stent of FIG. 3.

In use, ureteral stent 10 is inserted into a mammalian ureter 30 such that distal end 14 of elongated member 12 is in a kidney 32 and proximal end 18 is in bladder 34, as shown in FIG. 3. Ureteral stent 10 may be inserted with the aid of a guidewire and a pusher through the urethra (not shown) and bladder 34 to the final position in ureter 30. In some embodiments, first retention structure 16 and second retention structure 20 are formed from a material that reforms its structure after having its shape distorted. This property of the material allows first retention structure 16 and second retention structure 20 to be collapsed or straightened during insertion of the stent into the body, yet allowing the structures to reform into their original shapes after placement of ureteral stent 10 in ureter 30. The guidewire or a cannula may be used to temporarily straighten the retention structure during insertion and placement of ureteral stent 10. Ureteral stent 10 may also be inserted into position by use of an endoscope, a ureteroscope, or a cytoscope, for example.

Figure 4:
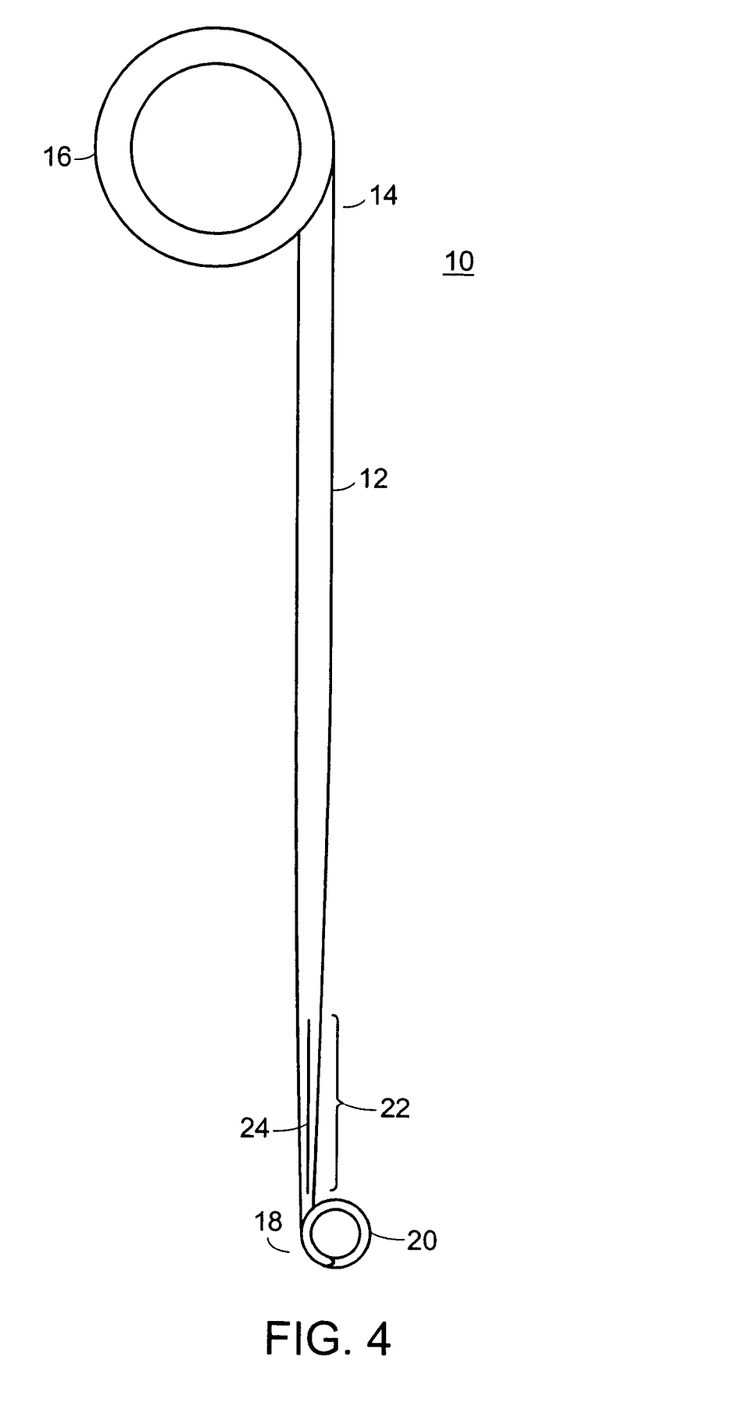
FIG. 4 depicts an exemplary ureteral stent with a slit valve in a tapered portion of the stent.

If proximal end 18 includes a second retention structure 20 shaped as a barb 20' (FIGS. 2A, 2B, 2D), the barb preferably engages ureteral orifice 36 to prevent ureteral stent 10 from migrating distally out of bladder 34. A cannula, sleeve, or cytoscope is preferably used to cover the barb during insertion of ureteral stent 10 into the patient. Desirably, as shown in FIG. 3, this configuration minimizes the amount of material from the ureteral stent 10 that resides in bladder 34 as compared to, for example, the amount of material from the first retention structure 16 shown residing in kidney 32. Thus, the potential for irritation to the trigone region 38 of bladder 34 is reduced. Valve 22 is preferably placed within intramural tunnel 40 of ureter 30. In embodiments where valve 22 includes window or windows 28, as shown in FIG. 3, or a slit or other modification reducing the resistance to kinking of the wall of that portion of elongated member 12, intramural tunnel 40 closes around the outer surface of the valve, activating it by collapsing its wall such that opposite walls contact one another and obstruct the lumen, preventing urine reflux during voiding of bladder 34. Thus, the positioning of valve 22 within intramural tunnel 40 minimizes irritation to intramural tunnel 40, reducing patient discomfort. To further reduce irritation to intramural tunnel 40, the portion of elongated member 12 intended for placement in intramural tunnel 40 may also be tapered (e.g. to a size of about 5 French) as shown in FIG. 4.

Figure 5A:
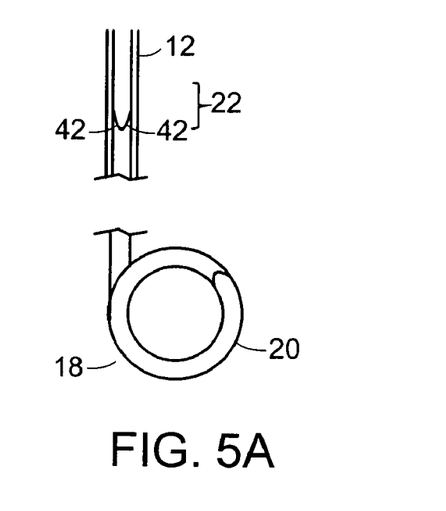
FIG. 5A depicts a stent with an internal flap valve and with a pigtail as a proximal retention structure.
Figure 5B:
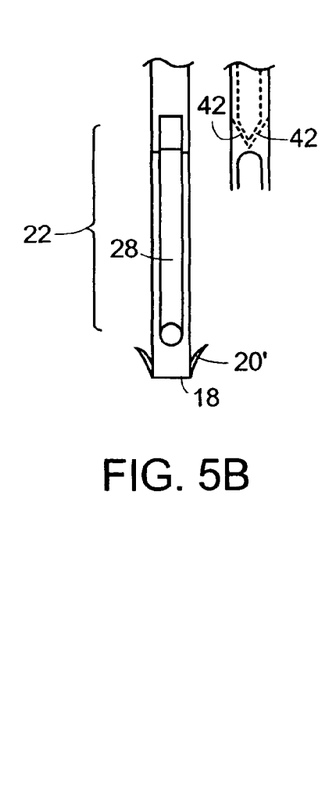
FIG. 5B depicts a proximal portion of a stent with large windows and a flap valve.

As shown in FIGS. 5A-5B, valve 22 may include at least one flap 42 (e.g. a pair of flaps 42, as shown) extending inward from an internal wall of elongated member 12 to better reduce urine reflux. The flap (or flaps) 42 contact a wall of elongated member 12 (and/or each other) to resist fluid flow from the bladder. The flap or flaps 42 nevertheless open to permit fluid drainage from the kidney.

Figure 6:
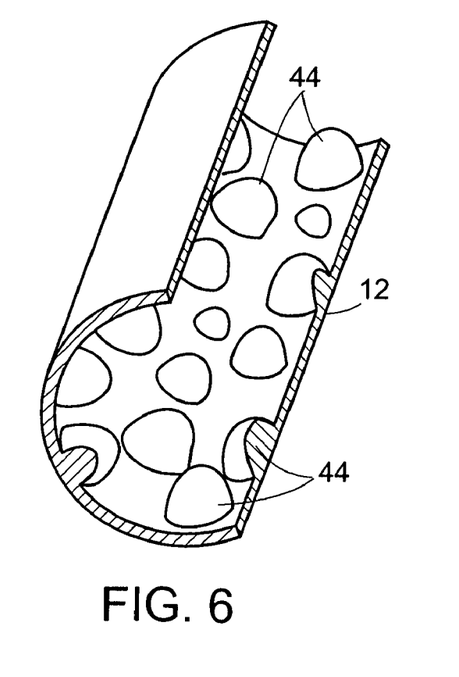
FIG. 6 depicts protrusions in a ureteral stent lumen.

Urine reflux may also be minimized a valve that includes one or more protrusions 44 as shown in FIG. 6. Protrusion(s) 44 extend from the inner surface of elongated member 12 into the lumen, partially occluding the lumen. Protrusion(s) 44 introduce turbulence into urine flow toward kidney 32 during voiding of bladder 34. Urine in bladder 34 is at a relatively high pressure during voiding, and would travel at relatively high speed toward a kidney through an open ureteral stent, in the absence of a valve, protrusion, or other mechanism to retard the urine reflux. Protrusion(s) 44 in ureteral stent 10 act as one or more "speed bumps" to absorb or deflect the energy or velocity of high pressure urine, slowing and (thereby) reducing urine reflux. Generally, protrusion(s) 44 increase(s) turbulence in refluxing urine, dissipating the energy of the urine flow. Protrusion(s) 44, which are preferably rigid, nevertheless do not preclude the normal flow of urine from the kidney to the bladder. Thus, in embodiments where a protrusion 44 spans the lumen of elongated member 12, one or more gaps or pores in protrusion 44 permit passage of urine therethrough. Protrusion(s) 44 reduce(s) the hydraulic radius of a portion of elongated member 12. Preferably, the protrusions are positioned and shaped to reduce the hydraulic radius by at least a factor of two, and more preferably by at least a factor of four. A discussion of factors determining the hydraulic radius of a channel and the effects of various types of protrusions on hydraulic radius may be found in Chapter 4 of Lindeburg, P. E., *Engineer In Training Review Manual*, Professional Publications: San Carlos, Calif. (1982), herein incorporated by reference.

Figure 7:
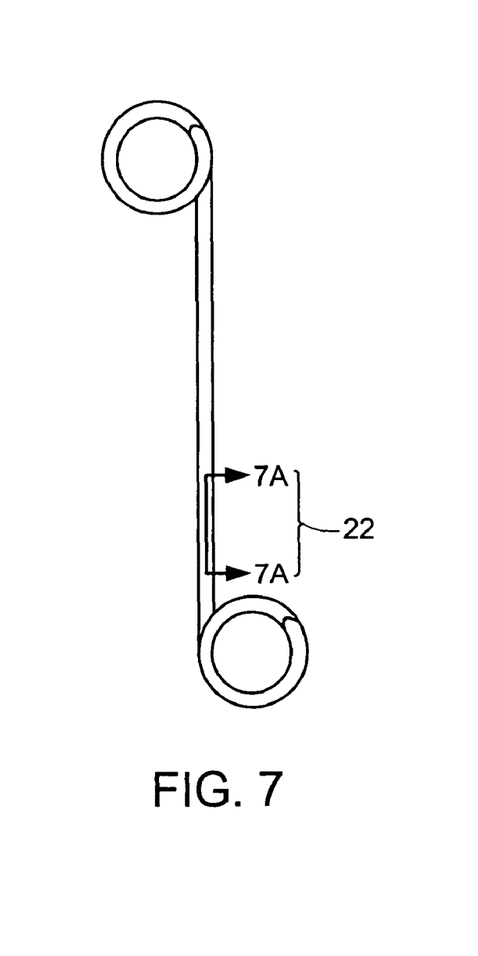
FIG. 7 depicts a helical thread protruding into a ureteral stent lumen.
Figure 7A:
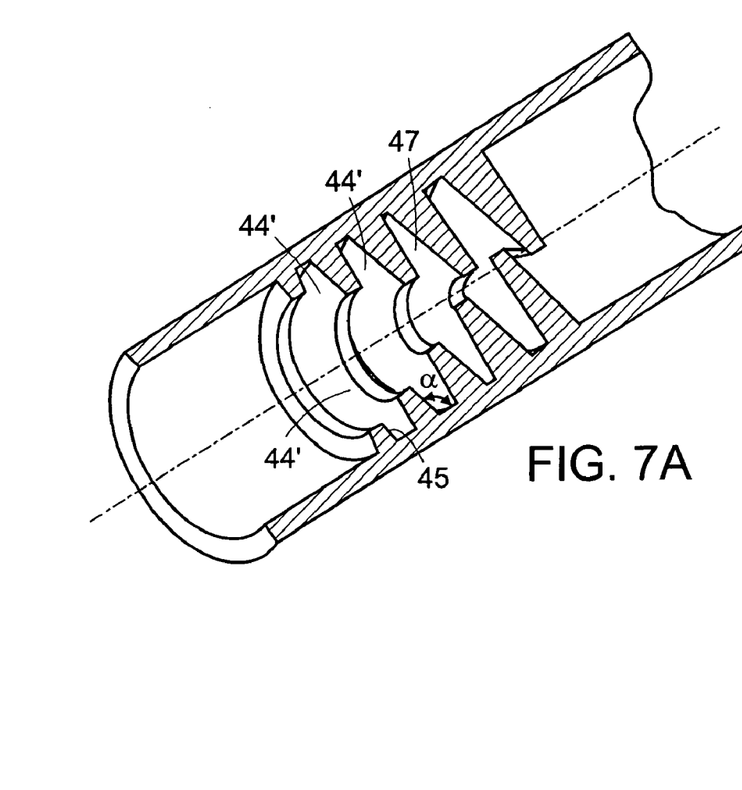
FIG. 7A is a partial cross-section view of the ureteral stent of FIG. 7 taken between 7A and 7A of FIG. 7.

Ureteral stent 10 may include a protrusion 44' shaped as a helical thread like an Archimedes' screw as shown in FIG. 7. Protrusion 44' need not extend throughout the length of ureteral stent 10; indeed, protrusion 44' is preferably limited to only a portion (e.g. a 1-3 cm portion) of ureteral stent 10. Preferably, the height of the thread/protrusion is varied along its length such that a portion of protrusion 44' closer to proximal end 18 of elongated member 12 has a height into the lumen that is greater than the height of a more distal portion of the protrusion 44'. In an embodiment where the lumen has a substantially circular cross-section, the height of a proximal portion of protrusion 44' is preferably greater than a radius of the lumen. Thus, fluid passing through the lumen necessarily follows the helical threads, because no line-of-sight fluid path is available. Generally, the sides of the protrusion form right and/or obtuse angles with the inner surface of the elongated member; the angles may be sharp or rounded. In one embodiment, a proximal surface 45 of protrusion 44' forms a right angle with the inner surface of elongated member 12. In another embodiment, a distal surface 47 of protrusion 44' forms an obtuse angle $\alpha$ with the inner surface of the elongated member 12.

Ureteral stent 10 with protrusion(s) 44 or 44' may be formed, for example, by injection molding the protrusion(s) or by lamination over an insert. The protrusion(s) may be formed of a metal or a polymer.

Figure 8A:
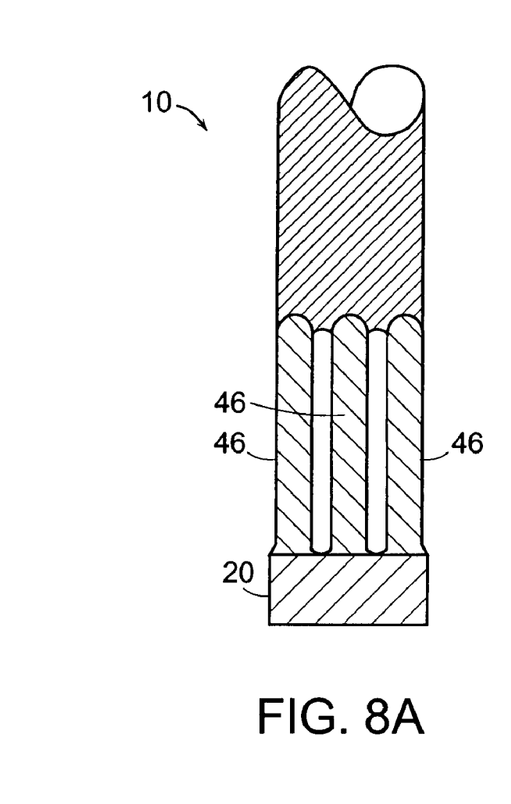
FIGS. 8A-8E depict ureteral stents having an expandable retention structure at the proximal end.
Figure 8B:
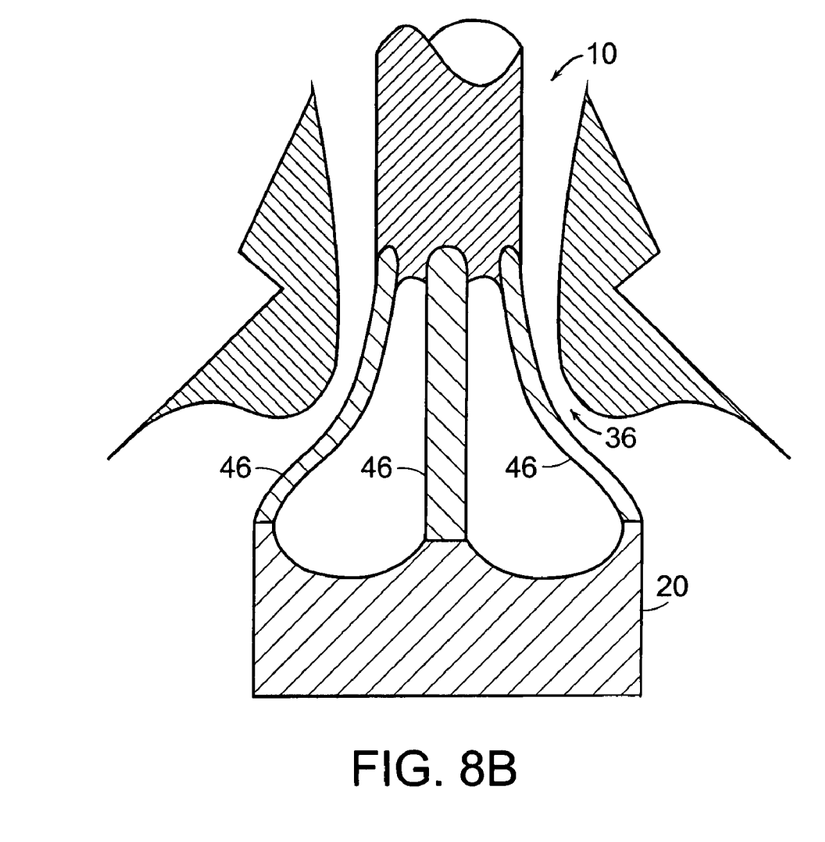
Figure 8C:
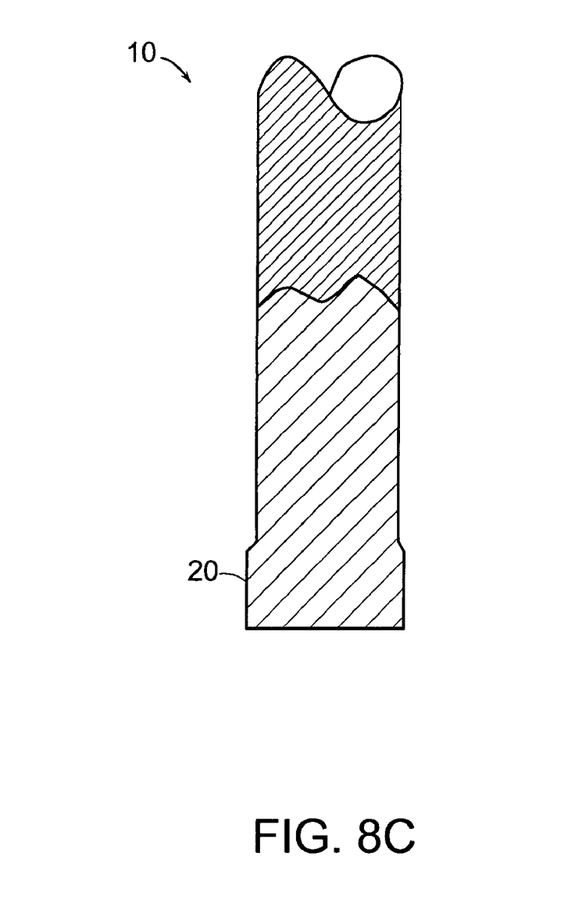

In preferred embodiments shown in FIGS. 8A-8E, second retention structure 20 includes a hydrophilic swellable polymer that expands upon hydration. Thus, as shown in FIGS. 8A and 8C, prior to hydration, second retention structure 20 may be as small as 5 to 9 French, ensuring that ureteral stent 10 can be delivered using standard stent delivery equipment (e.g. cytoscopes). Upon insertion of ureteral stent 10 into a ureter 30 (FIGS. 8B, 8D, and 8E), exposure of the hydrophilic polymer to moisture from urine causes significant hydration of the hydrophilic polymer, leading to expansion of second retention structure 20. Second retention structure 20 thus becomes larger than the opening of ureteral orifice 36. Thus, upon expansion of second retention structure 20, proximal end 18 of ureteral stent 10 is necessarily retained within bladder 34. Generally, expansion is substantially complete within about 1-2 hours. Expansion of second retention structure 20 also dramatically softens it from, for example, about 65D to about 35-40A. This softening should reduce irritation to trigone region 38 of bladder 34 (FIG. 8E), and facilitates stent extraction, as the material easily deforms through the urethra upon removal.

Despite the post-hydration expansion of second retention structure 20 in the preferred ureteral stent 10 shown in FIGS. 8A-8E, second retention structure 20 remains smaller in mass and surface area than a conventional stent bladder coil. Second retention structure 20 may be shaped as a cylinder, for example, or in any other shape, so long as, after expansion, second retention structure 20 is larger than the opening of ureteral orifice 36 in a dimension permitting retention of second retention structure 20 at ureteral orifice 36.

A hydrophilic swellable polymer, if present, may be any polymer capable of sufficient expansion upon hydration, such as, reticulated or crosslinked polymers derived from any of polyurethane, nylon, polycarbonate, poly(ethylene oxide), polyvinyl pyrrolidone, polyvinyl alcohol, poly(ethylene glycol), polyacrylamide, poly(hydroxyethylacrylate), and copolymers thereof. Generally, hydration expands the swellable polymer by at least a factor of 1.2. Preferably, outer diameter of the hydrophilic polymer expands at least a factor of 1.5 upon hydration; more preferably, the outer diameter expands by at least a factor of 2.0 upon hydration. Thus, for example, the outer diameter of second retention structure 20 may be about 0.08 inches prior to hydration, and about 0.16 inches or more after hydration. Useful hydrophilic polymers and their application in ureteral stents can be found, for example, in U.S. Pat. Nos. 5,599,291; and 5,964,744, both of which are herein incorporated by reference in their entirety.

Figure 8D:
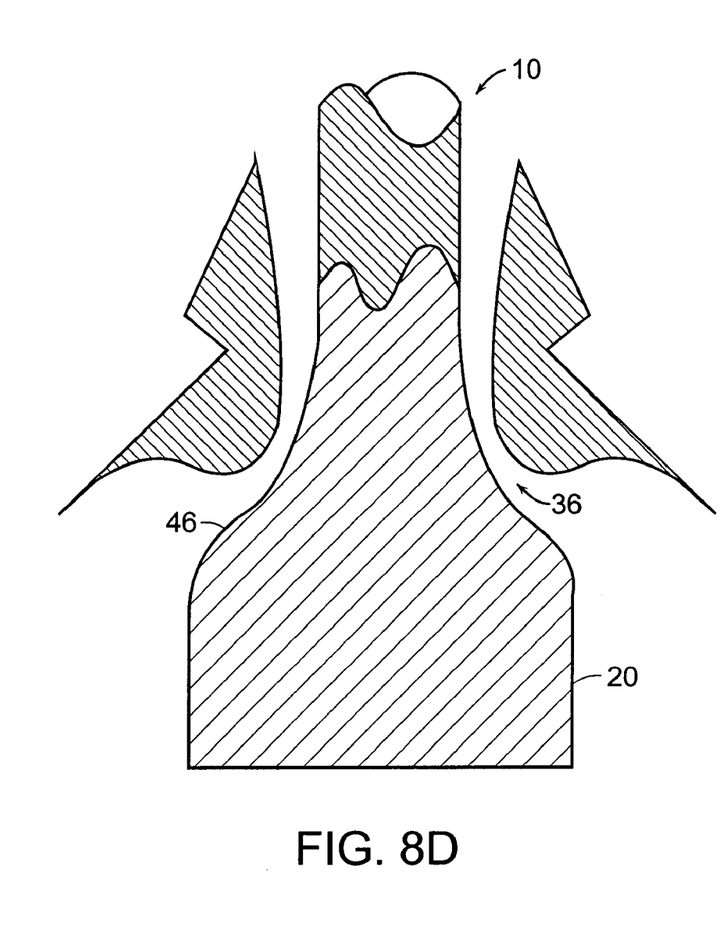
Figure 8E:
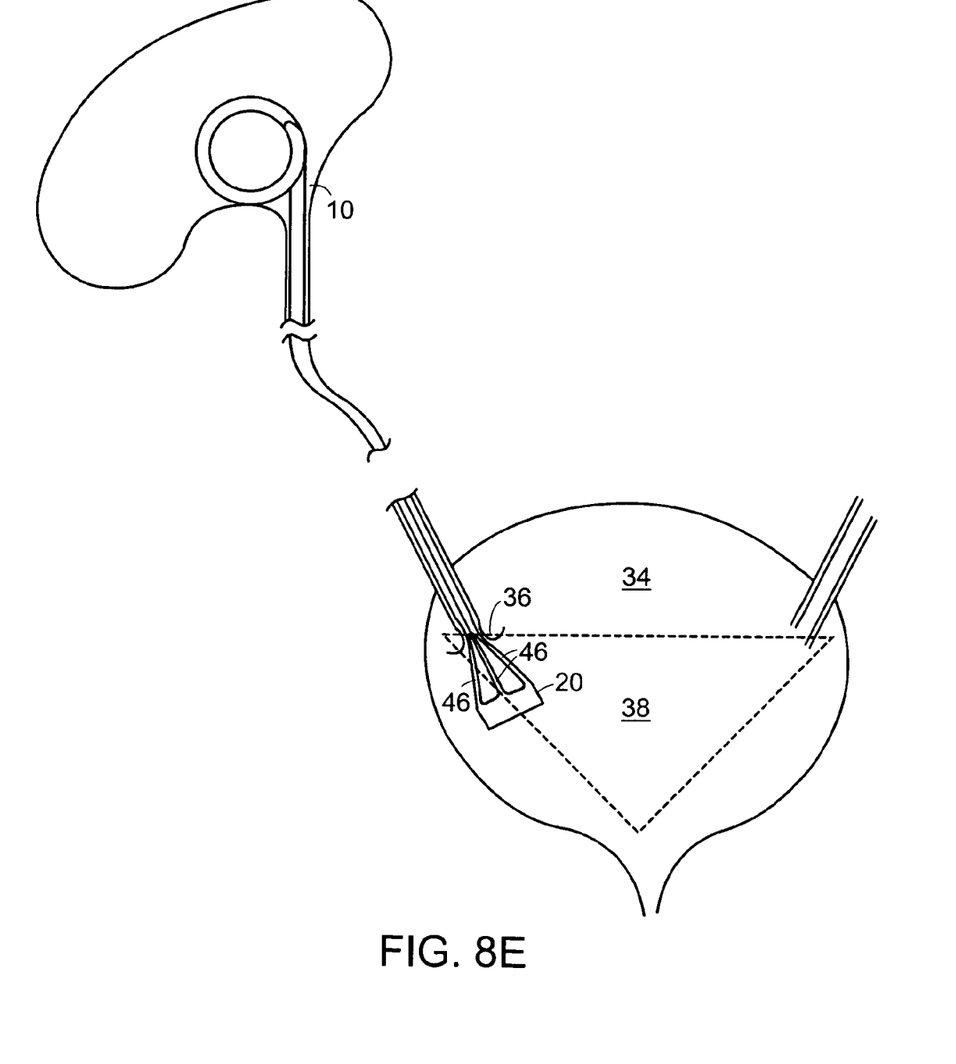

An expandable second retention structure 20 may be joined to the remainder of ureteral stent 10 through a plurality (e.g., 2-8) of connectors 46, as shown in FIGS. 8A, 8B, and 8E. In this embodiment, ureteral stent 10 transitions from a cylindrical extrusion to a series of solid-core polymer connectors 46 about 5 cm from the ureteral orifice. The cylindrical extrusion typically has an outer diameter of 5-8 French and an inner diameter of 0.04"-0.08"; the connectors 46 typically have outer diameters of about 0.01"-0.04." Connectors 46 may be attached to the remainder of ureteral stent 10 by a thermal attachment/lamination process, in which case connectors 46 should be thermally compatible with the hydrophilic polymer of second retention structure 20, and more preferably is formed of the same base polymer. Alternatively, connectors 46 may be formed by excising or otherwise removing material from a portion of a cylindrical extrusion, or may be incorporated into ureteral stent 10 using coextrusion techniques.

As shown in FIG. 8E, connectors 46 provide a collapsible proximal ureter/intramural tunnel section to reduce intramural tunnel irritation when compared to a conventional cylindrical stent portion. Because the intramural tunnel compresses about connectors 46 during voiding of bladder 34, urine reflux is diminished by the reduction in the "free-volume" available in the distal ureter.

Alternatively, second retention structure 20 may be attached directly to the remainder of ureteral stent 10 as shown in FIGS. 8C-8D, through thermal attachment procedures, for example. Even in the absence of connectors 46, second retention structure 20 is free to expand and function as intended in this alternative embodiment, preventing upward stent migration toward kidney 32 and providing a relatively soft portion in bladder 34 to reduce irritation to trigone region 38.

Elements of the ureteral stents of the present invention may be attached to each other by any of a variety of methods including, for example, the use of adhesives, heat welding, mechanical fasteners, and/or by inserting one component into the internal diameter of another. For example, two elements may be formed, one with a female end and one with a male end with teeth stamped therein, so that when the male end is inserted into the female end, it is locked or snap-fit into position with the teeth. Retention structures, such as pigtails, hooks, barbs, and/or lips, may be made of memory-shaped material so that the structures may be temporarily straightened for insertion along a guidewire and thereafter returned to their "normal" shapes.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of illustrative embodiments of the invention is not intended to be limiting.

What is claimed is:

1. A ureteral stent comprising:
   an elongated member having a distal end comprising a first retention structure extending away from a longitudinal axis defined by the elongated member and a proximal end comprising a second retention structure, the elongated member having an inner surface defining a lumen between the distal end and the proximal end; and
   a protrusion, having a first portion and a second portion extending circumferentially from the inner surface into the lumen to partially occlude the lumen, wherein the protrusion is shaped and positioned to introduce turbulence into urine flow from the proximal end during voiding of a bladder when the distal end is disposed in a kidney and the proximal end is disposed in the bladder, the protrusion extending more than one continuous revolution around the inner surface, the first portion of the protrusion having a first height, the second portion of the protrusion having a second height different from the first height, the first height being greater than a radius of the lumen such that the first portion of the protrusion overlaps the second portion of the protrusion, the first portion of the protrusion extending from a first location of the inner surface, the second portion of the protrusion extending from a second location of the inner surface opposite the first location.

2. The ureteral stent of claim 1, wherein:
   the height of the first portion of the protrusion is greater than a radius of the lumen defined by a portion of the inner surface from which the protrusion extends; and
   the height of the second portion of the protrusion is less than the radius of the lumen defined by the portion of the inner surface from which the protrusion extends.

3. The ureteral stent of claim 1, wherein the inner surface is substantially uniform and has a substantially circular cross-section.

4. The ureteral stent of claim 1, wherein the protrusion comprises a proximally-facing wall and a distally-facing wall, the proximally-facing wall forming a 90 degree angle with the inner surface.

5. The ureteral stent of claim 1, wherein:
   an outside surface of the elongated member is substantially uniform and has a substantially circular cross-section; and
   the inner surface is substantially uniform and has a substantially circular cross-section.

6. The ureteral stent of claim 1, where the protrusion comprises a proximally-facing wall and a distally-facing wall, the distally-facing wall forming an angle of more than 90 degrees with the inner surface.

7. The ureteral stent of claim 1, wherein the protrusion extends at least one revolution around the inner surface such that a fluid path from a bladder to a kidney through the lumen is extended by the protrusion.

8. The ureteral stent of claim 1, wherein the elongate member has a substantially constant thickness.

9. The ureteral stent of claim 1, wherein the protrusion extends at least two revolutions around the inner surface such that a fluid path from a bladder to a kidney through the lumen is extended by the protrusion.

10. The ureteral stent of claim 1, wherein an outer diameter of the elongated member is substantially constant.

11. A ureteral stent comprising:
    an elongated member having a distal end comprising a first retention structure extending away from a longitudinal axis defined by the elongated member and a proximal end comprising a second retention structure, the first retention structure and the second retention structure each being configured to be disposed within a body of a patient and configured to engage bodily tissue to help retain the ureteral stent in place within the body of the patient, the elongated member having an inner surface defining a lumen between the distal end and the proximal end; and
    a helical thread extending from a portion of the inner surface between the distal end and the proximal end, the helical thread having a height extending into the lumen, the height of the helical thread being greater than a radius of the lumen, the radius of the lumen defined by a portion of the inner surface from which the helical thread extends.

12. The ureteral stent of claim 11, wherein the height of a proximal portion of the helical thread is greater than the height of a distal portion of the helical thread.

13. The ureteral stent of claim 12, wherein the inner surface is substantially uniform and has a substantially circular cross-section.

14. The ureteral stent of claim 11, wherein the helical thread comprises a proximally-facing wall and a distally-facing wall, the proximally-facing wall forming a 90 degree angle with the inner surface.

15. The ureteral stent of claim 11, wherein a proximally-facing wall of the helical thread and a second wall of the helical thread form a sharp-edged angle no greater than about 90 degrees.

16. The ureteral stent of claim 11, wherein the helical thread comprises a proximally-facing wall and a distally-facing wall, the distally-facing wall forming an angle of more than 90 degrees with the inner surface.

17. The ureteral stent of claim 11, wherein the helical thread extends at least one revolution around the inner surface such that a fluid path from a bladder to a kidney through the lumen is extended by the helical thread.

18. The ureteral stent of claim 11, wherein:
    an outside surface of the elongated member is substantially uniform and has a substantially circular cross-section; and
    the inner surface is substantially uniform and has a substantially circular cross-section.

19. The ureteral stent of claim 11, wherein the height of the helical thread at a first portion of the helical thread extending from a first side of the inner surface is greater than a radius of the lumen such that the first portion of the helical thread overlaps a second portion of the helical thread extending from a second side of the inner surface opposite of the first side.

20. The ureteral stent of claim 11, wherein the elongate member has a substantially constant thickness.

21. The ureteral stent of claim 11, wherein:
    the height of the helical thread is at a proximal portion of the helical thread; and
    a height of the helical thread at a distal portion of the helical thread is less than the radius of the lumen.

22. The ureteral stent of claim 11, wherein the helical thread extends at least two revolutions around the inner surface such that a fluid path from a bladder to a kidney through the lumen is extended by the helical thread.

23. The ureteral stent of claim 11, where in an outer diameter of the elongated member is substantially constant.

24. A method comprising the steps of:
providing a ureteral stent comprising an elongated member having a distal end comprising a first retention structure extending away from a longitudinal axis defined by the elongated member and a proximal end comprising a second retention structure, the elongated member having an inner surface defining a lumen between the distal end and the proximal end, a protrusion extending circumferentially from the inner surface into the partially occluding the lumen such that the protrusion extends more than one continuous revolution around the inner surface, the protrusion having a height extending into the lumen greater than a radius of the lumen;
introducing the ureteral stent into a body of a patient such that the urethra stent extends from a kidney of the patient to a bladder of the patient; and
disrupting urine flow from the bladder to the kidney during voiding of the bladder through partial occlusion of the lumen, thereby reducing reflux.

25. The method of claim 24 wherein the introducing includes positioning the ureteral stent such that a proximal portion of the protrusion is toward the bladder and a distal portion of the protrusion is toward the kidney, thereby discouraging reflux of urine from the bladder to the kidney and permitting drainage of urine from the kidney to the bladder, the protrusion extending farther into the lumen at the proximal portion of the protrusion than at the distal portion of the protrusion.

26. A method comprising the steps of:
providing a ureteral stent comprising an elongated member having a distal end comprising a first retention structure extending away from a longitudinal axis defined by the elongated member and a proximal end comprising a second retention structure, the elongated member having an inner surface defining a lumen between the distal end and the proximal end, a helical thread having a height extending into the lumen from a portion of the inner surface, and wherein the height of a proximal portion of the helical thread is greater than the height of a distal portion of the helical thread;
introducing the ureteral stent into a body of a patient such that the urethra stent extends from a kidney of the patient to a bladder of the patient; and
positioning the helical thread to reduce urine flow from the bladder to the kidney during voiding of the bladder, thereby reducing reflux.

27. The method of claim 26, wherein the ureteral stent is positioned such that the height of the helical thread is greater in a portion of the thread toward the bladder, thereby discouraging reflux of urine from the bladder to the kidney and permitting drainage of urine from the kidney to the bladder.

* * * * *

UNITED STATES PATENT AND TRADEMARK OFFICE
CERTIFICATE OF CORRECTION

| | | |
|---|---|---|
| PATENT NO. | : 8,142,386 B2 | Page 1 of 1 |
| APPLICATION NO. | : 11/052099 | |
| DATED | : March 27, 2012 | |
| INVENTOR(S) | : John O. McWeeney | |

It is certified that error appears in the above-identified patent and that said Letters Patent is hereby corrected as shown below:

IN THE SPECIFICATIONS:

In column 1, line 6, delete "herby" and insert -- hereby --, therefor.

IN THE CLAIMS:

In column 9, line 16, in claim 1, delete "portion" and insert -- portion, --, therefor.

In column 9, line 54, in claim 6, delete "where" and insert -- wherein --, therefor.

In column 10, line 56, in claim 19, delete "of the" and insert -- the --, therefor.

In column 11, line 12, in claim 24, delete "the" and insert -- and --, therefor.

In column 11, line 18, in claim 24, delete "urethra" and insert -- ureteral --, therefor.

In column 12, line 17, in claim 26, delete "urethra" and insert -- ureteral --, therefor In column 12, line 24, in claim 27, after "thread" insert -- that is --.

Signed and Sealed this
Third Day of July, 2012

David J. Kappos
*Director of the United States Patent and Trademark Office*